United States Patent
Eiermann et al.

(12) 
(10) Patent No.: US 6,353,101 B1
(45) Date of Patent: Mar. 5, 2002

(54) METHOD FOR PRODUCING LACTAMS

(75) Inventors: Matthias Eiermann, Limburgerhof; Thomas Narbeshuber, Ludwigshafen, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/555,606

(22) PCT Filed: Nov. 30, 1998

(86) PCT No.: PCT/EP98/07717

§ 371 Date: May 31, 2000

§ 102(e) Date: May 31, 2000

(87) PCT Pub. No.: WO99/28296

PCT Pub. Date: Jun. 10, 1999

(30) Foreign Application Priority Data

Dec. 1, 1997 (DE) ......................................... 197 53 301

(51) Int. Cl.⁷ ............................................ C07D 201/08
(52) U.S. Cl. ....................................................... 540/539
(58) Field of Search ......................................... 540/539

(56) References Cited

U.S. PATENT DOCUMENTS 2,357,484 A * 9/1944 Martin ....................... 260/239
4,628,085 A   12/1986 Mares et al. ................ 540/539
5,493,021 A * 2/1996 Barratt et al. ............... 540/539
5,723,603 A * 3/1998 Gilbert et al. .............. 540/539

FOREIGN PATENT DOCUMENTS

FR  2029540    10/1970
WO  96/22974    8/1996

OTHER PUBLICATIONS

Derwent Abstract 96–362611/36 (English abstract of WO 96/22974).

Derwent Abstract 71–02568S (English abstract of FR 2029540).

* cited by examiner

*Primary Examiner*—Bruck Kifle
(74) *Attorney, Agent, or Firm*—Keil & Weinkauf

(57) ABSTRACT

The invention relates to a process for preparing lactams by cyclizing hydrolysis of amino nitriles with water in the gas phase on catalysts which comprise oxides or mixed oxides of the metals of groups 3, 4, 5, 13 and/or 14 of the Periodic Table, where appropriate in addition a metal oxide of groups 6, 7, 8, 9 and/or 10, and further comprise a phosphate, carbonate, silicate, arsenite, arsenate, antimonite, antimonate and/or nitrate of said metals and/or, if metal oxides of groups 6, 7, 8, 9 or 10 are present, a sulfate of the abovementioned metals.

8 Claims, No Drawings

METHOD FOR PRODUCING LACTAMS

The present invention relates to a process for preparing lactams by cyclizing hydrolysis of amino nitriles with water in the gas phase on metal oxide catalysts.

Lactams are compounds which can be employed in a variety of ways. For example, N-methylpyrrolidone is a versatile solvent and ε-caprolactam is an important monomer for polyamide fibers. Caprolactam is prepared industrially by a Beckmann rearrangement of the oxime of cyclohexanone. This reaction results in large amounts of salts, generally sodium sulfate, as byproduct which must be disposed of.

U.S. Pat. No. 2,357,484 discloses a process for preparing amides and lactams from the corresponding nitriles and amines, and the amino nitriles respectively, by gas-phase reaction with water on catalysts with dehydrating properties. Catalysts indicated as usable are, in particular, alumina, silica gel and boric/phosphoric acid.

WO 96/22974 describes a process for preparing lactams by cyclizing hydrolysis of amino nitriles, using alumina catalysts with a specific surface area of $\geq 10$ m$^2$/g and a pore volume (of pores with a diameter of more than 500 Å) $\geq 10$ ml/100 g.

U.S. Pat. No. 4,628,085 discloses a process for preparing lactams in the gas phase, where an aliphatic or aromatic amino nitrile and water are brought into contact with a silica-based catalyst with BET surface areas of more than 250 m$^2$/g and pore diameters of less than 20 nm in the presence of hydrogen and ammonia.

The use of metal phosphates, especially aluminum, zirconium, niobium and lanthanum phosphates, as catalysts for preparing lactams in the gas phase from amino nitriles and water is described in EP-A 659 741. These catalysts can also be impregnated with basic alkali metal or alkaline earth metal compositions, with cesium, rubidium and potassium being preferred.

EP-A 748 797 discloses a process for preparing lactams from dinitriles, where the dinitrile is hydrogenated to the amino nitrile, and the amino nitrile is converted into the lactam by cyclizing hydrolysis. Disclosed as catalyst for the cyclizing hydrolysis are molecular sieves such as acidic zeolites, silicates and non-zeolite molecular sieves, metal phosphates and metal oxides or mixed oxides, which are, where appropriate, acidic or amphoteric due to treatment with halogens, ammonium halides or acids such as sulfuric acid or hydrohalic acid.

The disadvantage of the described processes is that the selectivity of the catalysts is inadequate in some cases, which on the one hand makes it difficult to isolate the lactams, and on the other hand leads to poisoning of the catalysts by the byproducts which are formed. It is also desirable to increase the activity of the catalysts.

It is an object of the present invention to provide a process for preparing lactams by cyclizing hydrolysis of amino nitriles which affords them with high selectivity and high space-time yield and, moreover, allows a long useful life of the catalyst.

We have found that this object is achieved by reacting the amino nitriles with water on oxides of the metals of groups 3, 4, 5, 13 and/or 14 of the Periodic Table as catalysts which comprise a phosphate, carbonate, silicate, arsenite, arsenate, antimonite, antimonate or nitrate of said metals and, where appropriate, a metal oxide of groups 6, 7, 8, 9 and/or 10.

The present invention therefore relates to a process for preparing lactams by cyclizing hydrolysis of amino nitriles with water in the gas phase on metal oxide catalysts, wherein the catalysts comprise:

- at least one oxide or mixed oxide of the metals of groups 3, 4, 5, 13 and/or 14 of the Periodic Table,
- one or more oxides or mixed oxides of metals of groups 6, 7, 8, 9 and/or 10,
- at least one carbonate, silicate, phosphate, arsenite, arsenate, antimonite, antimonate and/or nitrate and/or when oxides or mixed oxides of metals of groups 6, 7, 8, 9 or 10 are present, a sulfate of the abovementioned metals.

The numbering of the groups of the Periodic Table in this specification is in accordance with the 1985 IUPAC proposal.

Catalysts preferred according to the invention are compounds of the formula I:

$$MQ_a(RO_b)_cO_d \qquad (I)$$

in which

M is Zr, Ti, Hf, Sc, Y, La, Ce, V, Nb or Ta, in particular Zr, Ti or Hf, and very especially Zr, R is P, C, Si, N, As or Sb, Q is a metal from group 6, 7, 8, 9 or 10, a is a number from 0 to 10, b is a number from 0.5 to 5, c is a number from 0.001 to 0.15, and d has the magnitude necessary to achieve neutrality of charge.

The catalysts comprise up to five molecules of water per formula unit. If a $\geq 0.001$, R can also be S.

Catalysts which are particularly preferably used are compounds of the formula I in which R is P or, if a $\geq 0.001$, can also be S, Q is Mn, a is 0 to 0.1 and very particularly preferably 0 to 0.03, and c is 0.001 to 0.1 and very particularly preferably 0.01 to 0.1, and particularly preferred compounds are those in which R is P and Q is Mn.

The catalyst materials can be employed in any suitable form such as, for example, as powder, as chips or else as shaped articles. Examples of shaped articles which are used are extrudates or beads. For the shaping, a binder can be added, such as, for example, Aerosil, potato starch or celluloses, for example Walocel supplied by Wolff-Walsrode AG, these binders not being present in stated formula I. It is likewise possible for the catalyst materials to be applied to a carrier such as, for example, alumina, silica gel, carbon, silicon carbide or silicon nitride. The catalyst is preferably used in the novel process in the form of chips or shaped articles.

The catalyst bed may be mixed with a component to increase the selectivity in amounts of from 0 to 70% by volume. Examples thereof are silicon dioxide, preferably quartz, silicon nitride and silicon carbide.

The catalysts are prepared in a manner known per se and familiar to the skilled worker. The novel catalysts can be obtained, for example, by contacting at least one oxide and/or hydroxide of a metal of groups 3, 4, 5, 13 and/or 14 of the Periodic Table one or more times with suitable phosphates, sulfates, carbonates, silicates, arsenites, arsenates, antimonites, antimonates or nitrates, and then calcining at elevated temperature. Suitable examples are the corresponding salts of metals of groups 3, 4, 5, 13 and 14 of the Periodic Table, the ammonium salts of oxo acids of these metals and, if desired, the salts of the metals of groups 6 to 10 of the Periodic Table, and phosphoric acid, sulfuric acid or nitric acid and their ammonium salts.

The contacting takes place, for example, by adding a solution of the required phosphate, carbonate, silicate, nitrate, arsenite, arsenate, antimonite, antimonate or sulfate, or of the corresponding free acid, to an aqueous suspension of the metal oxide or hydroxide of groups 3, 4, 5, 13 or 14, of the Periodic Table, and then removing the water. This procedure can be repeated. The required components can be brought into contact all at once or in separate steps with the suspension of the metal oxide. In place of the solutions of the abovementioned salts, it is also possible to employ solutions of different salts of these metals in sulfuric acid, phosphoric acid or nitric acid, which is diluted with water where appropriate, as long as the anion of these salts forms a volatile acid with the mineral acid. Suitable salts are thus also the halides and the acetates as long as these are employed in one of the abovementioned acids or in aqueous solutions of these acids.

The components can moreover be converted into a homogeneous solution from which a crude catalyst composition is obtained, for example by evaporation or by addition of a precipitant, and is then converted into the active form of the catalyst by drying and calcination.

A further possible procedure is to spray a molding of the metal oxide, such as pellets, beads, hemispheres or extrudates, with aqueous solutions of suitable salts or the free acids. This procedure can be repeated several times, as a rule carrying out drying steps between the individual impregnation steps.

In a preferred preparation process, the metals or metal oxides are brought into contact with one of the abovementioned free acids in a first step and then, after a drying step, if required, brought into contact with an aqueous solution of a suitable metal salt of groups 6 to 10 of the Periodic Table, in the case of manganese for example with $Mn(NO_3)_2$, $MnSO_4$, $MnHPO_4$, $MnCO_3$ or $MnCl_2$, the latter being employed in optionally dilute sulfuric, nitric or phosphoric acid. Drying and calcination are then carried out.

The procedure for preparing catalysts based on zirconium oxide (and analogously for the other metal oxides) which are doped with P can, for example, be to suspend commercially available zirconium oxide and/or zirconium hydroxide in water, bring the suspension into contact with dilute phosphoric acid or an aqueous ammonium phosphate solution, remove the water, for example by distillation under reduced pressure, and dry the residue. The crude catalyst composition obtainable in this way can be either directly calcined or further processed to shaped articles and then calcined. It is also possible for the drying step to be followed by another impregnation step with an aqueous solution of a salt of a metal of groups 6 to 10, for example a manganese salt.

The calcination is normally carried at from 500 to 900° C., preferably at about 700° C. in 5 to 25 hours, preferably 10 to 20 hours. During this there is conversion, for example, of $HPO_4^{2-}$ or $H_2PO_4^-$ into $P_2O_7^{4-}$ and other cyclic phosphates and of $HCO_3^-$ into $CO_3^{2-}$. However, this conversion preferably does not take place completely under the chosen conditions so that, for example on use of P, there is still $PO_4^{3-}$ remaining in the resulting catalyst.

The Zr contents of the individual catalysts, determined by X-ray fluorescence analysis (R. Bock: Methoden der analytischen Chemie, Bd. 2, Nachweis- und Bestimmungsmethoden Teil 1, Verlag Chemie, Weinheim 1980), are between 60 and 71 g, preferably between 65 and 70 g, per 100 g of catalyst. The P, S and Mn contents are determined by ICP (Inductively Coupled Plasma) atomic emission spectroscopy (A. Montasa, D. W. Golightly: Inductively Coupled Plasmas in Analytical Atomic Spectrometry, 2nd edition, Verlag Chemie, Weinheim). Typical values are P: 0.2 to 1 g/100 g; S: 0.1 to 1 g/100 g and Mn: 0.1 bis 5 g/100 g of catalyst.

Normally used in the novel process are amino nitriles of the formula II:

$$R^1HN-X-CN \qquad (II)$$

in which X is an alkylene unit having at least 2 and at most 20 atoms. As a rule, these are carbon atoms, but there may also be one or more, but preferably not more than three, boron, nitrogen, phosphorus, oxygen and/or sulfur atoms present at any position within the alkylene unit. Between the amino group of the general formula —$NR^1H$ and the nitrile group there are at least 2, and preferably 3 to 6, atoms, preferably carbon atoms. Examples of alkylene are ethylene, 1,2- and 1,3-propylene, 1,2-, 1,3-, 1,4-, 2,3-butylene and 2-methyl-1,3-propylene, 1,2-, 1,3-, 1,4-, 1,5-, 2,3-, 2,4-pentylene, 2-ethyl-1,3-propylene, 2,2-dimethyl-1,3-propylene and 2- or 3-methyl-1,4-butylene, 1,2-, 1,3-, 1,4-, 1,5- and 1,6-hexylene, 2-, 3- or 4-methyl-1,5-pentylene, 2,2- or 2,3-dimethyl-1,4-butylene, 2- or 3-ethyl-1,4-butylene, 2-ethyl-2-methyl-1,3-propylene and 2-propyl-1,3-propylene, 3-oxa- and 3-thia-1,5-pentylene. $R^1$ is hydrogen or a straight-chain or branched alkyl group having up to 20 carbon atoms. Examples of suitable alkyl groups are methyl, ethyl, propyl, isopropyl, n-butyl, sec-butyl, n-pentyl, n-hexyl and 2-ethylhexyl. Amino nitriles with linear alkylene units X with 3, 4, 5 or 6 carbon atoms and primary amino groups are preferably used, i.e. 4-aminobutyronitrile, 5-aminovaleronitrile, ε-aminocapronitrile and 7-aminoenanthonitrile, particularly preferably ε-aminocapronitrile. The ratio of water to amino nitrile can be in the range from 1 to 50 mol/mol, preferably from 1 to 15 mol/mol.

The reaction can be carried out either in an agitated or in a stationary catalyst bed. The gas-phase reaction is preferably carried out on a fixed bed. The fixed bed can be arranged, for example, as a single bed or else divided over several trays. In the latter case, it is possible to influence the composition and the physical properties of the reaction mixture between the trays in a beneficial manner, for example by adding reactants or inert gases or using, for example, heat exchangers. The fixed bed may additionally be arranged in one or more reaction chambers, e.g. in a tube bundle reactor.

The reaction temperature will usually be in the range from 200 to 550° C., preferably from 300 to 400° C. A temperature which is too low would make the evaporation of the starting material difficult, and, in addition, high conversions can be achieved only with difficulty under these conditions. If the temperatures are too high there is increased formation of byproducts and decomposition products.

The pressure can be in the range from 0.01 to 10 bar during the reaction. The reaction is preferably carried out under atmospheric pressure.

The reaction can also be carried out with the addition of inert gas, for example argon or nitrogen. The molar ratio of inert gas to amino nitrile can be, where appropriate, in the range from 0 to 100 mol/mol.

The discharge from the reactor usually contains not only the lactam as product but also unreacted amino nitrile and water, and ammonia or amine and, in small amounts, byproducts such as amino carboxamides. The lactam can be isolated therefrom in a manner known per se, for example by distillation, extraction or crystallization.

Typically, from 50 to 2000 g, preferably more than 500 g, of amino nitrile/l of catalyst and hour are fed into the reactor.

The amino nitrile conversions are then in the range from 70 to 99.9%. The selectivity for lactam formation is, as a rule, above 85% based on amino nitrile employed. Selectivities achieved with preferred catalysts are also ≧90% and, in particular, ≧93%. These figures are even reached after the catalyst has been in use for several hundred hours.

The following examples are intended to illustrate the novel process without, however, restricting the scope of the invention.

EXAMPLES

I. Preparation of the Catalysts

The starting material used for preparing the catalysts was a commercially available, moist zirconium hydroxide in the form of a coarse powder. The following catalysts were prepared:

Catalyst A (as disclosed in U.S. Pat. No. 2,357,484)

167 g of dried $Zr(OH)_4$ are compacted with 5% Walocel (Wolff-Walsrode AG) and 67 ml of $H_2O$ in a kneader for 45 min and then shaped to 2 mm extrudates under a pressure of 55 bar. The extrudates are then predried at 50 to 110° C. for 3.5 h and calcined at 700° C. for 16 h, and then crushed.

Zr: 70.5 g/100 g

Catalyst B 55 g of dried $Zr(OH)_4$ are impregnated with 1.05 g of $H_3PO_4$ (85%) and 250 ml of $H_2O$, the water is stripped off in a rotary evaporator in vacuo, and the resulting product is calcined at 550° C. for 16 h.

Catalyst C 55 g of dried $Zr(OH)_4$ are impregnated with 3.49 g of $H_3PO_4$ (85%) and 250 ml of $H_2O$, the water is stripped off in a rotary evaporator in vacuo, and the resulting product is calcined at 700° C. for 16 h.

Catalyst D 50 g of dried $Zr(OH)_4$ are impregnated with 1.31 g of $H_3PO_4$ (85%) and 400 ml of $H_2O$. The water is stripped off in a rotary evaporator in vacuo, and the resulting product is dried at 180° C. for 16 h. Impregnation is carried out with a solution of 5.1 g of $Mn(NO_3)_2 \cdot 4H_2O$ in 250 ml of $H_2O$, the water is stripped off in a rotary evaporator in vacuo, and calcination is carried out at 700° C. for 16 h.

Zr: 66 g/100 g

P: 0.21 g/100 g

Mn: 0.68 g/100 g

Catalyst E 50 g of dried $Zr(OH)_4$ are impregnated with 1.31 g of $H_3PO_4$ (85%) and 400 ml of $H_2O$. The water is stripped off in a rotary evaporator in vacuo, and the resulting product is dried at 180° C. for 16 h. Impregnation is carried out with a solution of 1 g of $Mn(NO_3)_2 \cdot 4H_2O$ in 250 ml of $H_2O$, the water is stripped off in a rotary evaporator in vacuo, and calcination is carried out at 700° C. for 16 h.

Zr: 67.5 g/100 g

P: 0.9 g/100 g

Mn: 0.7 g/100 g

Catalyst F 162 g of dried $Zr(OH)_4$ are impregnated with 2.62 g of $H_3PO_4$ (85%) and 400 ml of $H_2O$. The water is stripped off in a rotary evaporator in vacuo, and the resulting product is dried at 180° C. for 16 h. Impregnation is carried out with a solution of 2 g of $Mn(NO_3)_2 \cdot 4H_2O$ in 400 ml of $H_2O$, and the water is stripped off in a rotary evaporator in vacuo. The product obtained in this way is compacted with 5% Walocel and 46 ml of water in a kneader for 30 min and shaped under a pressure of 35 bar to extrudates which are dried at 110° C. for 3.5 h and then calcined at 700° C. for 16 h.

Zr: 66.5 g/100 g

P: 0.68 g/100 g

Mn: 0.42 g/100 g

Catalyst G 50 g of dried $Zr(OH)_4$ are impregnated with 4.9 g of $(NH_4)_2SO_4$ and 400 ml of $H_2O$. The water is stripped off in a rotary evaporator in vacuo, and the resulting product is dried at 180° C. for 16 h. Impregnation is carried out with a solution of 5.1 g of $Mn(NO_3)_2 \cdot 4H_2O$ in 250 ml of $H_2O$, the water is stripped off in a rotary evaporator in vacuo, and calcination is carried out at 700° C. for 16 h.

Zr: 65 g/100 g

S: 0.63 g/100 g

Mn: 3 g/100 g

Catalyst H 50 g of dried $Zr(OH)_4$ are impregnated with 1.6 g of $(NH_4)_2SO_4$ and 250 ml of $H_2O$. The water is stripped off in a rotary evaporator in vacuo, and the resulting product is dried at 180° C. for 16 h. Impregnation is carried out with a solution of 1 g of $Mn(NO_3)_2 \cdot 4H_2O$ in 250 ml of $H_2O$, the water is stripped off in a rotary evaporator in vacuo, and calcination is carried out at 700° C. for 16 h.

These catalysts were tested in an electrically heated tubular reactor with an internal diameter of 30 mm, which was packed with 20 ml of catalyst as ≧1 mm chips, in some cases with the addition of 20 ml of quartz chips. The reactor was operated with downward flow, and 50 ml of quartz chips or quartz rings were introduced as vaporization zone above the catalyst. ε-Amino-capronitrile was fed in a 50% strength aqueous solution at 750 g/l of catalyst and hour. The reaction took place at 360° C. with the addition of 10 l of nitrogen per hour as carrier gas under atmospheric pressure. The conversion of ε-aminocapronitrile (ACN) and the selectivity for caprolactam (CPL) were determined by gas chromatography with internal standard and from the mass balance. The determinations were carried out after the reaction had remained stable for at least two days, after 165 h with A, after 254 h with B, after 90 h with C, after 65 h with D, after 95 h with E, after 768 h with F, after 97 h with G and after 122 h with H. Samples were collected for at least 12 h for analysis. The results are compiled in Table 1.

TABLE 1

| No. | Catalyst | Doping | CPL selectivity | ACN conversion |
|---|---|---|---|---|
| 1 | A |  | 89.6 | 98.8 |
| 2 | B | $PO_4$ | 91.6 | 99.3 |
| 3 | C | $PO_4$ | 94.4 | 99.6 |
| 4 | D | $PO_4$ + Mn | 93.4 | 96.5 |
| 5 | E | $PO_4$ + Mn | 98.4 | 99.5 |
| 6 | F | $PO_4$ + Mn | 94.3 | 98.0 |
| 7 | G | $SO_4$ + Mn | 97.4 | 72.3 |
| 8 | H | $SO_4$ + Mn | 97.4 | 87.4 |

It is evident that higher selectivities for caprolactam formation are achieved by the impregnated catalysts from the novel process.

We claim:

1. A process for preparing ε-aminocapronitrile by cyclizing hydrolysis of amino nitriles of formula II $$R^1HN\text{—}X\text{—}CN \qquad (II)$$

wherein X is a linear alkylene unit of 5 carbon atoms, and $R^1$ is H, with water in the gas phase on metal oxide catalysts, wherein the metal oxide catalysts used are compounds of the formula I:

$$MQ_a(RO_b)_cO_d \quad (I)$$

in which

M is Zr,

R is P,

Q is a metal from group 6, 7, 8, 9 or 10, a is a number from 0 to 0.1, b is a number from 0.5 to 5, c is a number from 0.001 to 0.15, and d has the magnitude necessary to achieve neutrality of charge, where R can also be S if a $\geq 0.001$.

2. The process of claim 1, wherein the ratio of water to amino nitrile is in the range from 1 to 50 mol/mol.

3. The process of claim 1, wherein the cyclizing hydrolysis reaction is performed at a temperature in the range from 200 to 550° C.

4. The process of claim 3, wherein the temperature is in the range from 300 to 400° C.

5. The process of claim 1, wherein the reaction is carried out under pressures in the range from 0.01 to 10 bar.

6. The process of claim 1, wherein from 50 to 2000 g of amino nitrile are fed per liter of catalyst and hour into the reactor.

7. The process of claim 6, wherein the amino nitrile is fed in an amount of more than 500 g per liter of catalyst and hour.

8. The process of claim 1, wherein Q denotes Mn and a is a number from 0.001 to 0.1.

* * * * *

UNITED STATES PATENT AND TRADEMARK OFFICE
CERTIFICATE OF CORRECTION

PATENT NO.    : 6,353,101 B1
DATED         : March 5, 2002
INVENTOR(S)   : Eiermann et al.

Page 1 of 1

It is certified that error appears in the above-identified patent and that said Letters Patent is hereby corrected as shown below:

Column 6,
Line 64, "ϵ-aminocapronitrile" should be -- ϵ-caprolactam --.

Signed and Sealed this

Twenty-seventh Day of August, 2002

Attest:

Attesting Officer

JAMES E. ROGAN
Director of the United States Patent and Trademark Office